US010324090B2

(12) United States Patent
Sreevatsan et al.

(10) Patent No.: US 10,324,090 B2
(45) Date of Patent: Jun. 18, 2019

(54) ***MYCOBACTERIUM* BIOMARKERS AND METHODS**

(71) Applicants: REGENTS OF THE UNIVERSITY OF MINNESOTA, Minneapolis, MN (US); Srinand Sreevatsan, Roseville, MN (US); Elise Lamont, Saint Paul, MN (US)

(72) Inventors: Srinand Sreevatsan, Roseville, MN (US); Elise Lamont, Saint Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 15/037,838

(22) PCT Filed: Nov. 21, 2014

(86) PCT No.: PCT/US2014/066782

§ 371 (c)(1),
(2) Date: May 19, 2016

(87) PCT Pub. No.: WO2015/077541

PCT Pub. Date: May 28, 2015

(65) Prior Publication Data

US 2016/0291012 A1 Oct. 6, 2016

Related U.S. Application Data

(60) Provisional application No. 61/907,686, filed on Nov. 22, 2013.

(51) Int. Cl.

| | |
|---|---|
| ***C12Q 1/00*** | (2006.01) |
| ***A61K 39/02*** | (2006.01) |
| ***A61K 39/04*** | (2006.01) |
| ***G01N 33/569*** | (2006.01) |
| ***G01N 33/92*** | (2006.01) |
| ***G01N 21/65*** | (2006.01) |

(52) U.S. Cl.
CPC ....... *G01N 33/5695* (2013.01); *G01N 21/658* (2013.01); *G01N 33/92* (2013.01); *G01N 2333/35* (2013.01); *G01N 2405/00* (2013.01); *G01N 2800/50* (2013.01)

(58) Field of Classification Search
CPC ......... A61K 39/00; A61K 39/02; A61K 39/04
USPC .................. 424/234.1, 248.1; 435/4, 7.1, 7.2
See application file for complete search history.

(56) References Cited

FOREIGN PATENT DOCUMENTS

WO WO2006/117538 * 11/2006
WO WO 2006/117538 A2 11/2006

OTHER PUBLICATIONS

Seth, M., et al. "Biomarker Discovery in Subclinical Mycobacterial Infections of Cattle". PLoS ONE, vol. 4, Issue 5, e5478, pp. 1-13, May 2009.*
International Search Report and Written Opinion issued for PCT/US2014/066782 by the European Patent Office as the International Search Authority; dated Jul. 14, 2015: 14 pgs.
International Preliminary Report on Patentability issued for PCT/US2014/066782 by the International Bureau of WIPO; dated Jun. 2, 2016; 9 pgs.
Antognoli et al., "Analysis of the diagnostic accuracy of the gamma interferon assay for detection of bovine tuberculosis in U.S. herds," *Prev Vet Med*, 2011;101:35-41.
Blanco et al., "Increased IL-17 expression is associated with pathology in a bovine model of tuberculosis," *Tuberculosis* (*Edinb*), 2011; 91:57-63.
Chen et al., "Role and regulation of bacterial LuxR-like regulators," *J Cell Biochem*, 2011; 112(10):2694-2702.
Chopra et al., "Polyketide versatility in the biosynthesis of complex mycobacterial cell wall lipids," *Methods Enzymol*, 2009; Chapter 12;459:259-294.
Cordials et al., "Detecting the immune system response of a 500 year-old Inca mummy," *PLoS One*, 2012; 7:e41244: 9 pgs.
Dohoo et al., "Veterinary Epidemiologic Research," VER Inc., 2010. Prince Edward Island, Canada. Cover page, title page and table of contents.
Essey et al., "Status of bovine tuberculosis in North America," *Vet Microbiol*, May 1994; 40(1-2):15-22.
Firdessa et al., "High prevalence of bovine tuberculosis in dairy cattle in central Ethiopia: implications for the dairy industry and public health," *PLoS One*, 2012;7:e52851.
Gaborick et al., "Evaluation of a five-antigen ELISA for diagnosis of tuberculosis in cattle and Cervidae," *J Am Vet Med Assoc.*, Sep. 1, 1996;209(5):962-966.
Garnier et al., "The Complete Genome Sequence of *Mycobacterium bovis," Proc Natl Acad Sci USA*; Jun. 24, 2003;100(13):7877-7882.
Green et al., "Rapid diagnosis of tuberculosis through the detection of mycobacterial DNA in urine by nucleic acid amplification methods," *Lancet Infect Dis*, Aug. 2009; 9:505-511.
Kohler et al., "Immune reactions in cattle after immunization with a *Mycobacterium paratuberculosis* vaccine and implications for the diagnosis of *M. paratuberculosis* and *M. bovis* infections," *J Vet Med B Infect Dis Vet Public Health*, Apr. 2001; 48(3):185-195.
Lamont et al., "Mannosylated lipoarabinomannanin serium as a biomarker candidtate for subclinical bovine tuberculosis," *BMC Research Notes*, Aug. 21, 2014;7(1):559.

(Continued)

*Primary Examiner* — Rodney P Swartz
(74) *Attorney, Agent, or Firm* — Mueting, Raasch & Gebhardt, PA

(57) ABSTRACT

This disclosure provides a method for detecting infection of an animal by *Mycobacterium bovis*. The method generally includes obtaining a biological sample from a host animal at risk of being infected by *Mycobacterium bovis* and analyzing the sample for the presence or absence of at least one *M. bovis* polypeptide. In some embodiments, the method can further include analyzing the sample for the presence or absence of at least one *M. bovis* lipid. In some embodiments, the method can further include detecting at least one host polypeptide whose expression is greater in a host infected with *M. bovis* compared to expression in a host known to be uninfected with *M bovis*.

36 Claims, 13 Drawing Sheets

(56) References Cited

OTHER PUBLICATIONS

Lamont et al., "Circulating *Mycobacterium bovis* Peptides and Host Response Proteins as Biomarkers for Unambiguous Detection of Subclinical Infection," *J Clin Microbiol*, Feb. 1, 2014;52(2):536-543.
Lee et al., "Genetic polymorphisms and susceptibility to lung disease," *J Negat Results Biomed*, 2006; 5:5: 11 pgs.
Pollock et al., "Validation of *Mycobacterium tuberculosis* Rv1681 protein as a diagnostic marker of active pulmonary tuberculosis," *J Clin Microbiol*, May 2013; 51(5): 1367-1373.
Sathyavathi et al., "Raman spectroscopy provides a powerful, rapid diagnostic tool for the detection of tuberculous meningitis in ex vivo cerebrospinal fluid samples," *J Biophotonics*, 2012; 6(8):567-572.
Stabel et al., "Pathogenesis of *Mycobacterium avium* subsp. *paratuberculosis* in neonatal calves after oral or intraperitoneal experimental infection," *Vet Microbiol.*, 2009;136:306-313.
Tanaka et al., "Identification of tuberculosis-associated proteins in whole blood supernatant," *BMC Infect Dis*, 2011., 11:71: 10 pgs.
Thacker et al., "Improved specificity for detection of *Mycobacterium bovis* in fresh tissues using IS6110 real-time PCR," *BMC Vet Res*, 2011; 7:50: 5 pgs.
USDA-APHIS. 2005. Bovine Tuberculosis Eradication: Uniform methods and rules, effective Jan. 1, 2015. Animal and Plant Health Inspection Service, U.S. Dept of Agriculture, Washington DC.: 35 pgs.
USDA—Agriculture—APHIS, Apr. 2008. Johne's disease on U.S. dairies, 1991-2007. In USDA-APHIS (ed.): 4 pgs.
USDA-APHIS. *Assessment of risk factors for Mycobacterium bovis in the United States.* USDA:APHIS: VS, Centers for Epidemology and Animal Health. Fort Collins, CO., Nov. 1992. Cover page, title page and table of contents; 3 pgs.
Wadhwa et al., "Bead-based microfluidic immunoassay for diagnosis of Johne's disease," *J Immunol Methods*, Aug. 31, 2012; 382(1-2):196-202.
Waters et al., "Tuberculosis immunity: opportunities from studies with cattle," *Clinical & Developmental Immunology*, 2011; 2011:768542: 11 pgs.
Waters et al., "Immune responses to defined antigens of *Mycobacterium bovis* in cattle experimentally infected with *Mycobacterium kansasii," Clinical and Vaccine Immunology: CVI*, Jun. 2006 13(6):611-619.
Waters et al., "Evaluation of gamma interferon (IFN-gamma)-induced protein 10 responses for detection of cattle infected with *Mycobacterium bovis:* comparisons to IFN-gamma responses," *Clinical and vaccine immunology: CVI*, Mar. 2012: 19(3):346-351.
Waters et al., "Immune responses in cattle inoculated with *Mycobacterium bovis, Mycobacterium tuberculosis*, or *Mycobacterium kansasii," Clinical and vaccine immunology: CVI*, Feb. 2010: 17:247-252.
Whipple et al., "Comparison of purified protein derivatives and effect of skin testing on results of a commercial gamma interferon assay for diagnosis of tuberculosis in cattle," *J Vet Diagn Invest*, Mar. 2001;13(2):117-122.
Williams et al., Functional analysis of molybdopterin biosynthesis in mycobacteria identifies a fused molybdopterin synthase in *Mycobacterium tuberculosis, J Bacteriol*, Jan. 2011; 193(1):98-106.
Zimin et al., "A whole-genome assembly of the domestic cow, *Bos taurus," Genome Biol*, Apr. 24, 2009; 10:R42: 10 pgs.
Zinsstag et al., "Economics of bovine tuberculosis," In C. O. Theon, J. H. Steele, and M. J. Gilsdorf (ed.), *Mycobacterium bovis infection in animals and humans.* Blackwell Publishing, Boston, MA. 2nd edition, 2006; p. 68-83.

* cited by examiner

Vitamin D Binding Protein (VDBP)

| Scenario | Pks5 Cutpoint | Se | Sp | LR+ | LR- |
|---|---|---|---|---|---|
| 1 | 0.2 | 1 | 0.75 | 4.0 | 0.0 |
| 2 | 0.3 | 0.99 | 0.90 | 9.9 | 0.0 |
| 3 | 0.4 | 0.92 | 0.93 | 13.1 | 0.1 |
| 4 | 0.5 | 0.79 | 0.95 | 15.8 | 0.2 |

A)

Area Under the Curve

Test Result Variable(s): Test

| Area | Std. Error[a] | Asymptotic Sig.[b] | Asymptotic 95% Confidence Interval | |
|---|---|---|---|---|
| | | | Lower Bound | Upper Bound |
| .983 | .022 | .000 | .941 | 1.000 |

a. Under the nonparametric assumption b. Null hypothesis: true area = 0.5

B)

Area Under the Curve

Test Result Variable(s): Test

| Area | Std. Error[a] | Asymptotic Sig.[b] | Asymptotic 95% Confidence Interval | |
|---|---|---|---|---|
| | | | Lower Bound | Upper Bound |
| .949 | .035 | .000 | .880 | 1.000 |

a. Under the nonparametric assumption b. Null hypothesis: true area = 0.5

B)

*MYCOBACTERIUM* BIOMARKERS AND METHODS

CROSS-REFERENCE TO RELATED APPLICATION

This application is the § 371 U.S. National Stage of International Application No. PCT/US2014/066782, filed 21 Nov. 2014, which claims priority to U.S. Provisional Patent Application Ser. No. 61/907,686, filed Nov. 22, 2013, each of which is incorporated herein by reference.

GOVERNMENT FUNDING

This invention was made with government support under 2009-34427.19959 awarded by the USDA. The government has certain rights in the invention.

SUMMARY

This disclosure provides, in one aspect, a method for detecting infection of an animal by *Mycobacterium bovis*. The method generally includes obtaining a biological sample from a host animal at risk of being infected by *Mycobacterium bovis* and analyzing the sample for the presence or absence of at least one *M. bovis* polypeptide.

In some embodiments, the biological sample can include serum, plasma, urine, or a fecal extract.

In some embodiments, the *M. bovis* polypeptide does not cross-react with serum from a host animal infected with another *Mycobacterium* spp. In some of these embodiments, the other *Mycobacterium* spp. can include *M. avium* subsp. *paratuberculosis*. In other embodiments, the other *Mycobacterium* spp. can include *M. kansasii.*

In some embodiments, the *M. bovis* polypeptide can include MB1895c, MB2515c, MB0862, MB1482c, MB2883c, MB1929, MB1192 MB1886c, MB2441c, MB2275, MB2122c, MB1672c, MB3729c, MB1268, MB3017c, or Pks5.

In some embodiments, the method can further include detecting at least one host polypeptide whose expression is greater in a host infected with *M. bovis* compared to expression in a host known to be uninfected with *M. bovis*. In some of these embodiments, the host polypeptide can include vitamin D binding protein (VDBP), fetuin-A.

In some embodiments, the method can further involve analyzing the sample for the presence or absence of at least one *M bovis* lipid. In some of these embodiments, the *M bovis* lipid can include lipoarabinomannan.

In some embodiments, the host animal can have a subclinical *M. bovis* infection.

In some embodiments, the host animal can exhibit no symptoms or clinical sign of infection by *M. bovis.*

In some embodiments, the method may be performed in a field location. In some of these embodiments, the method may be performed using a microfluidic device. In other embodiments, the method may be performed using portable surface-enhanced Raman spectroscopy.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
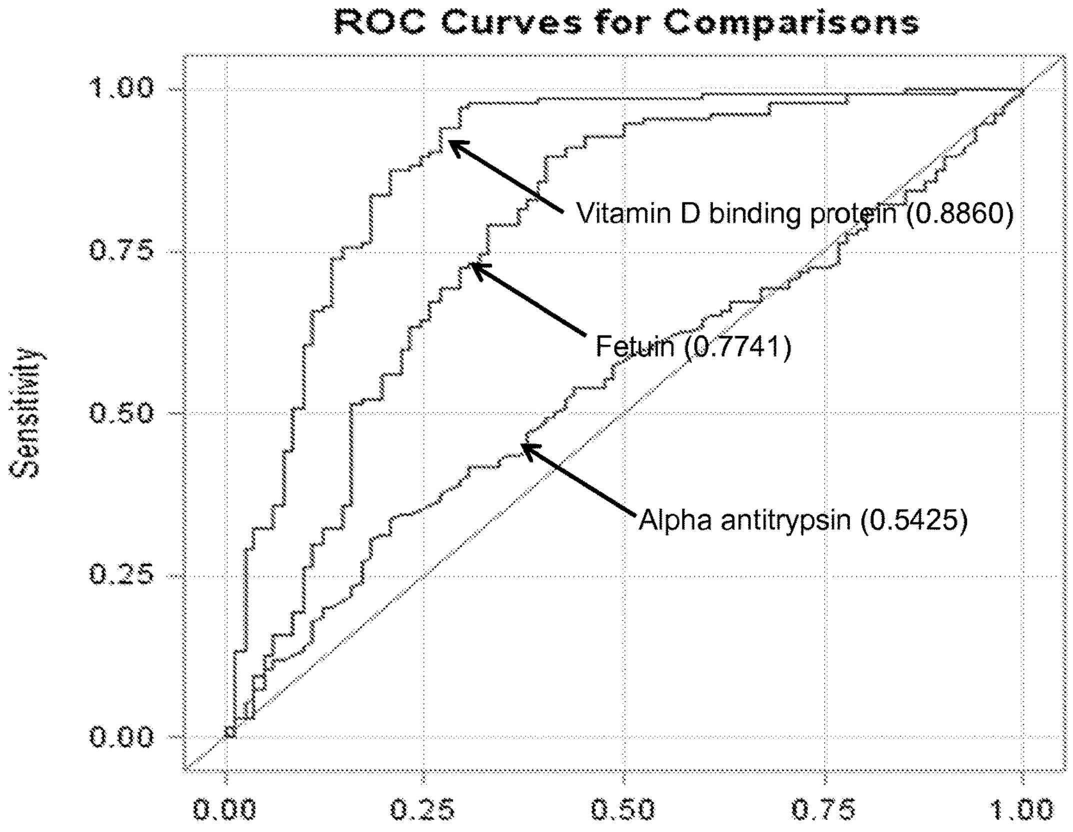
FIG. 1: Receiver Operating Characteristic (ROC) curves for host biomarkers. Each point on ROC curves is the fraction of bTB (bovine tuberculosis) positive cattle (true-positive rate) versus the corresponding fraction of negative exposed bTB cattle (false-positive rate). VDBP is the most reliable biomarker (AUC=0.8860), fetuin-A is a moderately reliable biomarker (AUC=0.7741), and alpha-1 antitrypsin is an unreliable biomarker (AUC=0.5425).

One element to preventing and/or control of bovine tuberculosis (bTB) is early and unambiguous identification of subclinical infection. Many diagnostics for subclinical infections rely on immune responses, which may be confounded by previous exposure to the suspect pathogen and/or cross-reactivity to similar microbes. This disclosure describes compositions and methods that permit one to detect subclinical infection by *Mycobacterium bovis*. The compositions and methods involve *M. bovis*-specific molecular signatures that may be detected in individuals with a subclinical *M. bovis* infection. The *M. bovis*-specific molecular signature can include one or more *M. bovis* polypeptide and/or *M. bovis* lipid.

Bovine tuberculosis, a prevalent disease of cattle worldwide caused by *Mycobacterium bovis*, is one example of detection failure and misidentification using conventional technologies. The United States Department of Agriculture (USDA) bTB eradication program relies on three main tests: caudal fold test (CFT), comparative cervical test (CCT), and a γ-interferon release assay (IGRA, Bovigam, Prionics AG, Schlieren, Switzerland) (USDA-APHIS. 2005. Bovine Tuberculosis Eradication. 35). All three tests are labor intensive, have logistical challenges, and sensitivity/specificity issues. For example, CFT lacks biological specificity for *M. bovis* infection and often fails to detect all diseased cattle, which can be further confounded by high background infection with a different pathogenic *mycobacterium, M. avium* subsp. *paratuberculosis*. In addition, IGRAs require blood processing within 24 hours of collection, which may not be feasible on large herds located in areas where a specialized laboratory is not easily accessible. Current testing limitations, significant economic losses, and spillover to human and wildlife populations highlight the urgency for a multifaceted test that increases detection, limits disease exposure, and distinguishes *M. bovis* infection from other mycobacteria and diseases that impact animal and human health.

The public availability of the genomes of cattle and *M. bovis* have advanced our understanding of host responses to *M. bovis* and its genetic elements that may be regulated during infection (Garnier et al. 2003. *Proc Natl Acad Sci USA* 100:7877-7882). Host responses utilized for conventional bTB diagnostics include an array of cytokines, chemokines, and antibody responses to *M. bovis* proteins. Although these tools provide another layer of testing, results obtained are often confounded by cross-reactivity due to homology between mycobacterial species. Furthermore, host response testing often relies on a single cut-off value for detection, which may not be applicable to the testing needs of all environments. For example, endemic bTB regions may require diagnostics with a high sensitivity to eliminate all infected cattle to control disease spread, while areas of low bTB prevalence may seek increased specificity to minimize false positives and avoid unnecessary economic losses.

Identification of *M. bovis* Polypeptides

In order to minimize cross-reactivity, we have identified 32 host and 16 pathogen circulating peptides, unique to *M. bovis* infection over a five-month follow-up of experimentally infected calves, using a highly sensitive proteomics approach (Seth et al. 2009. *PLoS One* 4:e5478). During infection, mycobacteria specific proteins, peptides, DNA, and lipids are shed into circulation and are likely to provide unprecedented specificity to identify *M. bovis* infection. A panel of biomarkers that includes host and pathogen peptides can establish a precise test to detect subclinical bTB infection. Serum host proteins (vitamin D binding protein (VDBP), fetuin-A, alpha-1 antitrypsin) and three pathogen peptides (MB1895c, MB2515c, and Pks5) were identified by iTRAQ and validated using a well characterized cattle serum repository including confirmed cases of *M. bovis*, negative bTB exposed (animals in contact with bTB positive cattle), and negative controls. Based on our findings, we describe methods, compositions, and kits for identifying circulating pathogen peptides and host response proteins in sera that may augment diagnostics and track disease progression across the spectra for other pathogenic infections.

VDBP Distinguishes Confirmed bTB From Uninfected and Exposed Cattle

Figure 2:
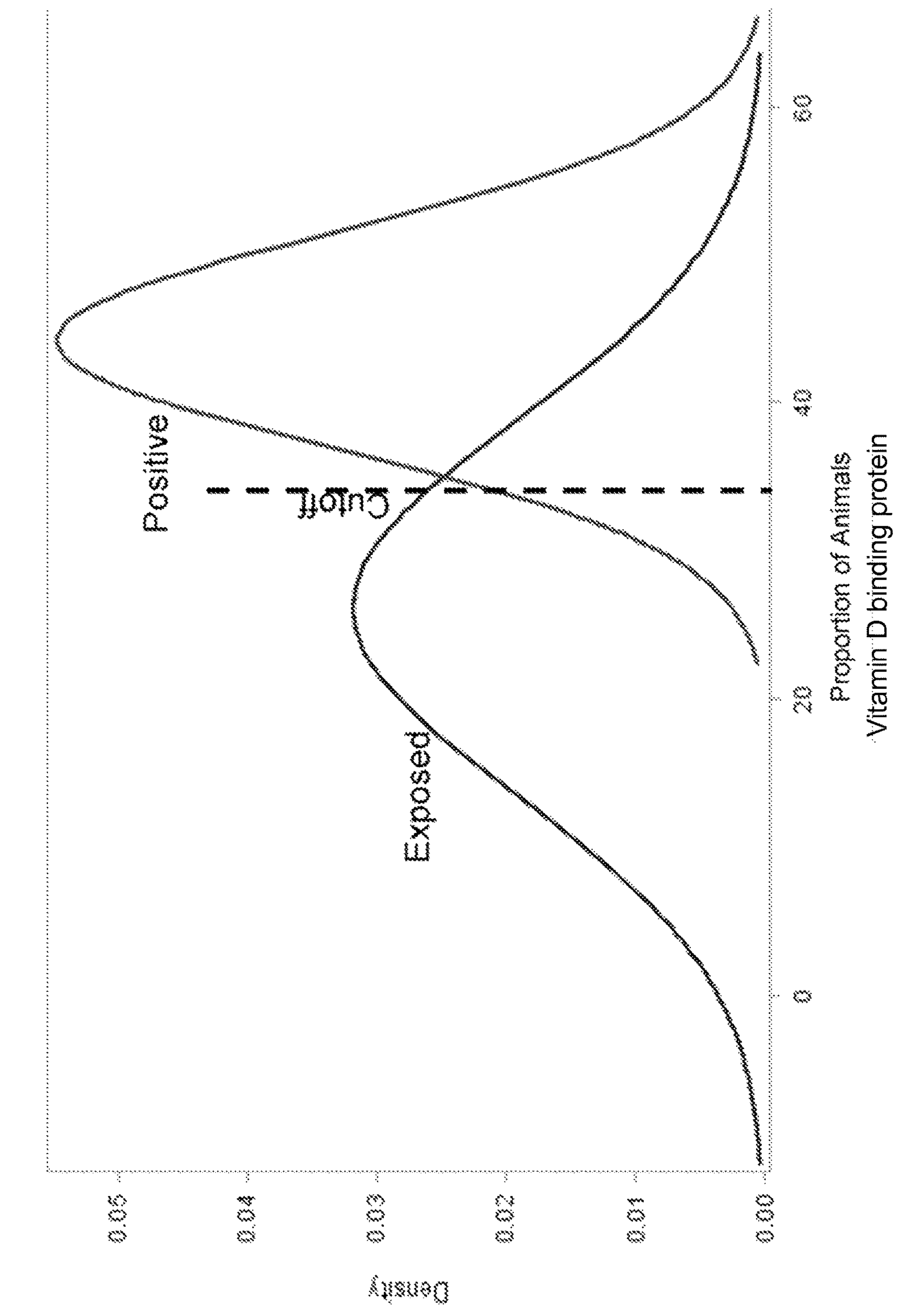
FIG. 2: Vitamin D binding protein (VDBP) histogram. Relative densities were collected from negative bTB exposed (n=82) and infected (n=128) animals. Cutoff value (38.50) was determined based on ROC analysis and true negative rate versus true positive rate.
Figure 3:
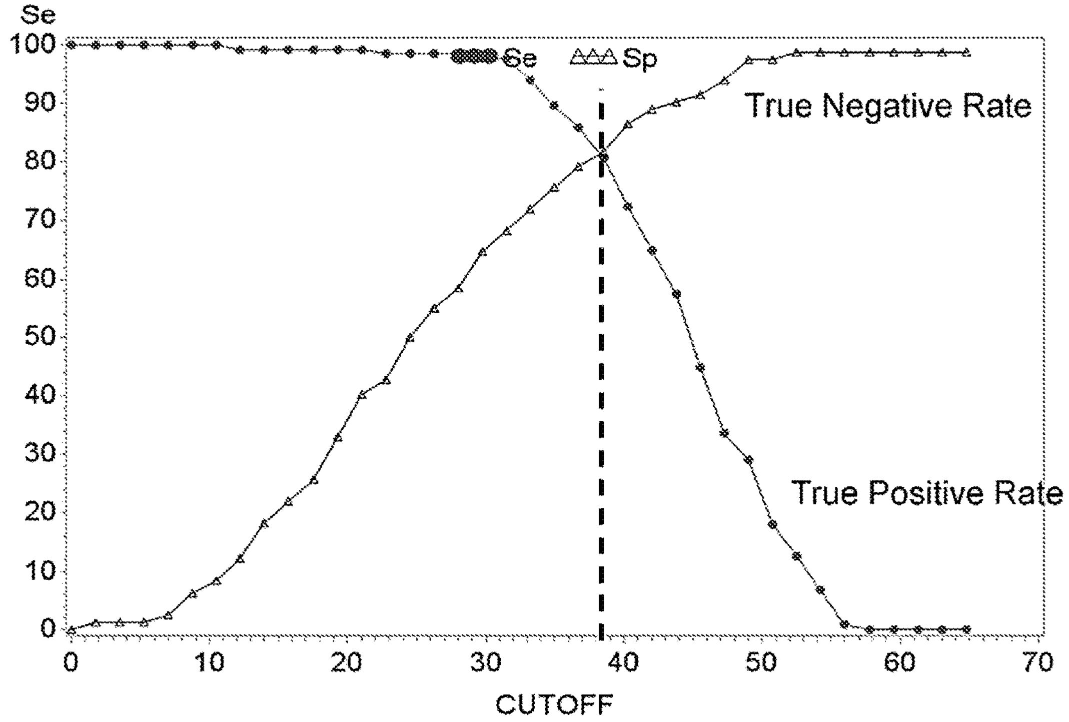
FIG. 3: Vitamin D Binding Protein distinguished bovine tuberculosis positive and negative exposed animals. The true negative rate and true positive rate using VDPB as a biomarker were plotted against each other. The optimal cutoff value corresponded to 38.50 (raw density). Cutoff value corresponds to a sensitivity of 80.6% and specificity of 81.7%.

The top three candidates identified by our previous study, alpha-1 antitrypsin, fetuin A, and VDBP, were validated for diagnostic potential in a large scale screen of control and *M. bovis* infected cattle. A total of 248 animals (negative control [n=38], confirmed bTB [n=128], and negative bTB exposed [n=82]) were tested for reactivity to alpha-1 antitrypsin, fetuin A, and VDBP via dot blot analysis. The area under the Receiver Operating Characteristic (ROC) curves (AUC) determined that VDBP was the most reliable biomarker capable of differentiation of negative, *M. bovis* infected, and negative bTb exposed animals (FIGS. 1-3, FIG. 7). Similar to VDPB, ROC curve analysis of fetuin-A showed a near perfect separation (0.9949) between negative controls and bTB infected animals; however, separation between negative bTB exposed and infected animals decreased to 0.7741 (FIG. 1). Although analysis of alpha-1 antitrypsin AUC exhibited a separation value of 0.7967 for infected versus uninfected animals, separation between infected and exposed groups could not be distinguished (AUC=0.5425) (FIG. 1). Herds suspected of bTB will unlikely include pristine animals (i.e., those that are uninfected and unexposed). Therefore, we examined VDBP as a potential diagnostic marker as the AUC for infected versus exposed animals was 0.8860 (FIG. 1). ROC analysis identified 5 cutoff ODs that retained high sensitivity and specificity, which ranged from 33.25-40.25 nm. The true negative rate and true positive rate were plotted against the OD cutoffs and the optimal cutoff value was 38.50 nm with a sensitivity of 80.597% and specificity of 81.7073% (FIGS. 2-3). Together these data show that VDBP is a reliable host biomarker that distinguishes negative, exposed, and bTb infected animals.

iRAQ Identification of *M. bovis* Specific Proteins in Serum

Sera from five *M. bovis* infected calves at one and four months post-infection and uninfected controls were pooled and analyzed by iTRAQ. Peptides were compared against the *M. bovis* strain AF2122/97 genome. iTRAQ analysis identified 16 unique *M. bovis* proteins present in sera from calves at 4 months PI (CI=95%) (Table 1).

TABLE 1

| Proteins identified in sera from *M. bovis* calves four months post-infection. | | |
|---|---|---|
| Locus ID | predicted function | subcellular location |
| MB2515c | transcriptional regulator (LuxR family) | Cytoplasm |
| MB0862 | methyltransferase activity | Cytoplasm |
| MB1482c | glucose metabolism | Cytoplasm |
| MB2883c | aldehyde dehydrogenase activity | Cytoplasm |
| MB1929 | redox activity | Cytoplasm |
| MB1886c | redox activity | Cytoplasm |
| MB1192 | hydrolase activity | Cytoplasm |
| MB2441c | hydrolase activity | Cytoplasm |
| MB2275 | FAD binding activity | Cytoplasm |
| MB2122c | transcriptional regulator | Cytoplasm |
| MB1672c | conserved hypothetical protein | Cytoplasm |
| MB1554c (pks5) | cell wall biosynthesis | Cytoplasm |
| MB1895c | molybdenum ion binding | Extracellular |
| MB3729c | conserved hypothetical protein | Periplasm |
| MB1268 | transporter activity | Transmembrane |
| MB3017c | isomerase activity | Transmembrane |

Figure 4:
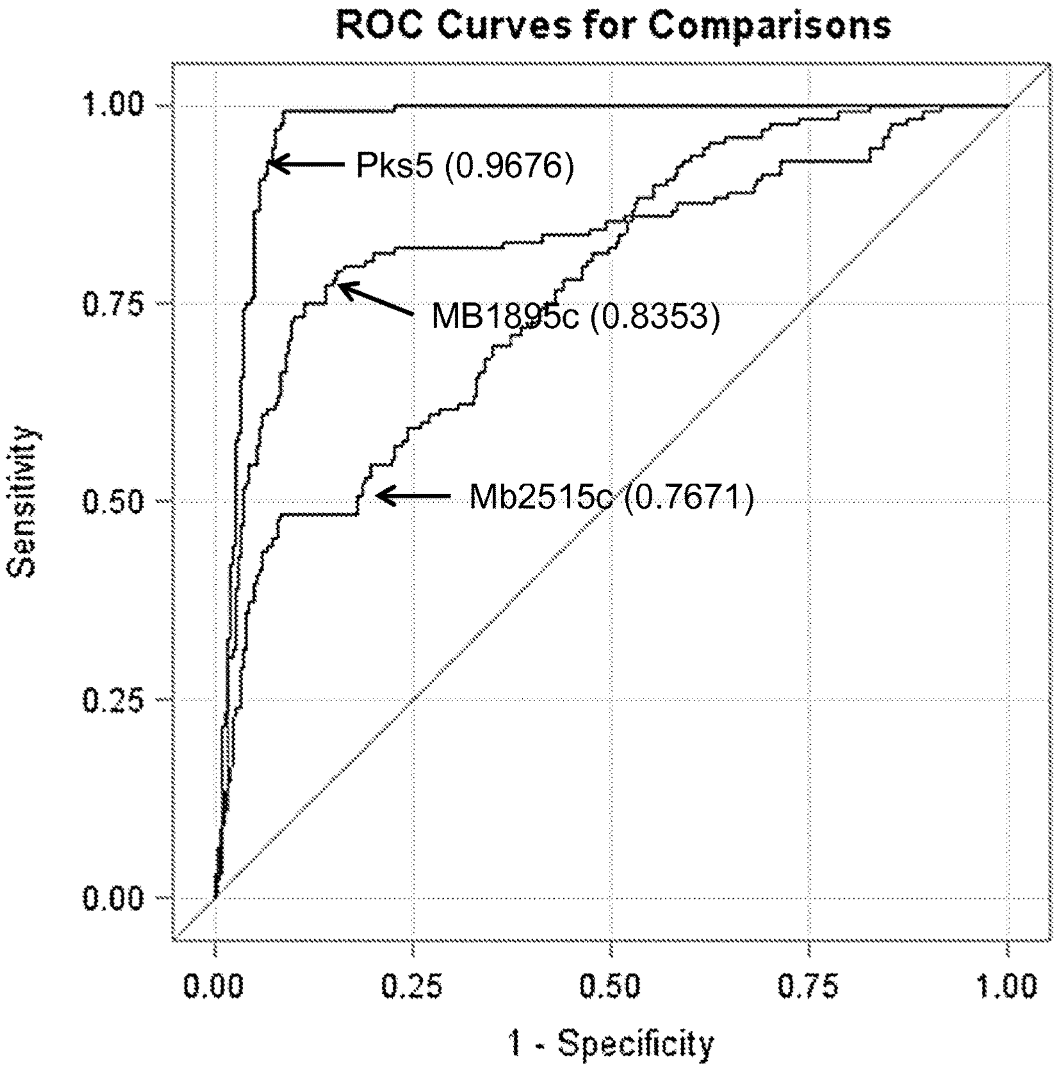
FIG. 4: Receiver Operating Characteristic (ROC) curves for pathogen biomarkers. Each point on ROC curves is the fraction of bTB positive cattle (true-positive rate) versus the corresponding fraction of negative exposed bTB cattle (false-positive rate). Pks5 is the most reliable biomarker (AUC=0.9676) and MB18952 and MB2515c are moderately reliable biomarkers (AUC=0.8353 and 0.7671, respectively).
Figure 5:
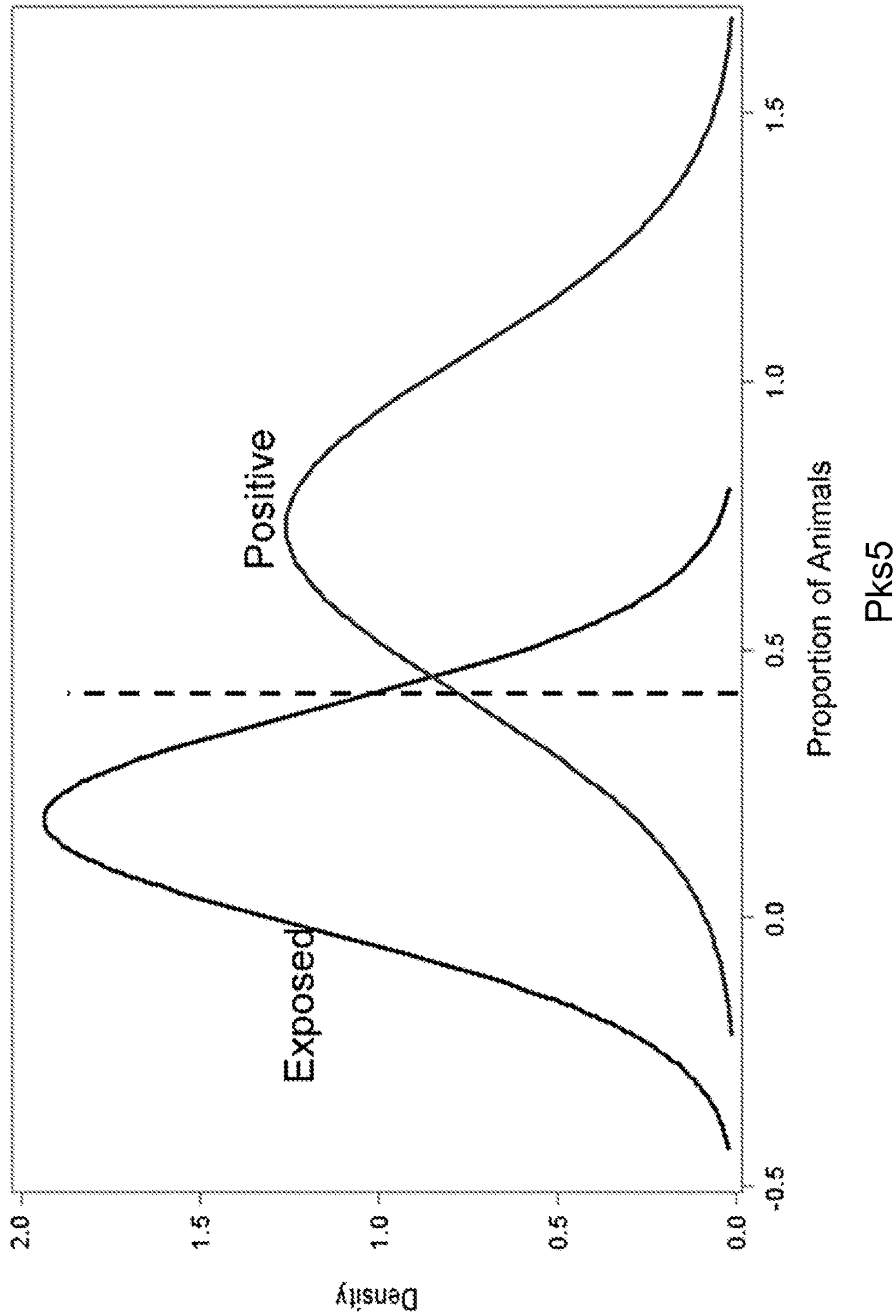
FIG. 5: Polyketide synthetase 5 (Pks5) histogram. Relative densities were collected from negative bTB exposed (n=428) and infected (n=128) animals. Cutoff value (0.4 nm) was determined based on ROC analysis and true negative rate versus true positive rate.
Figure 6:
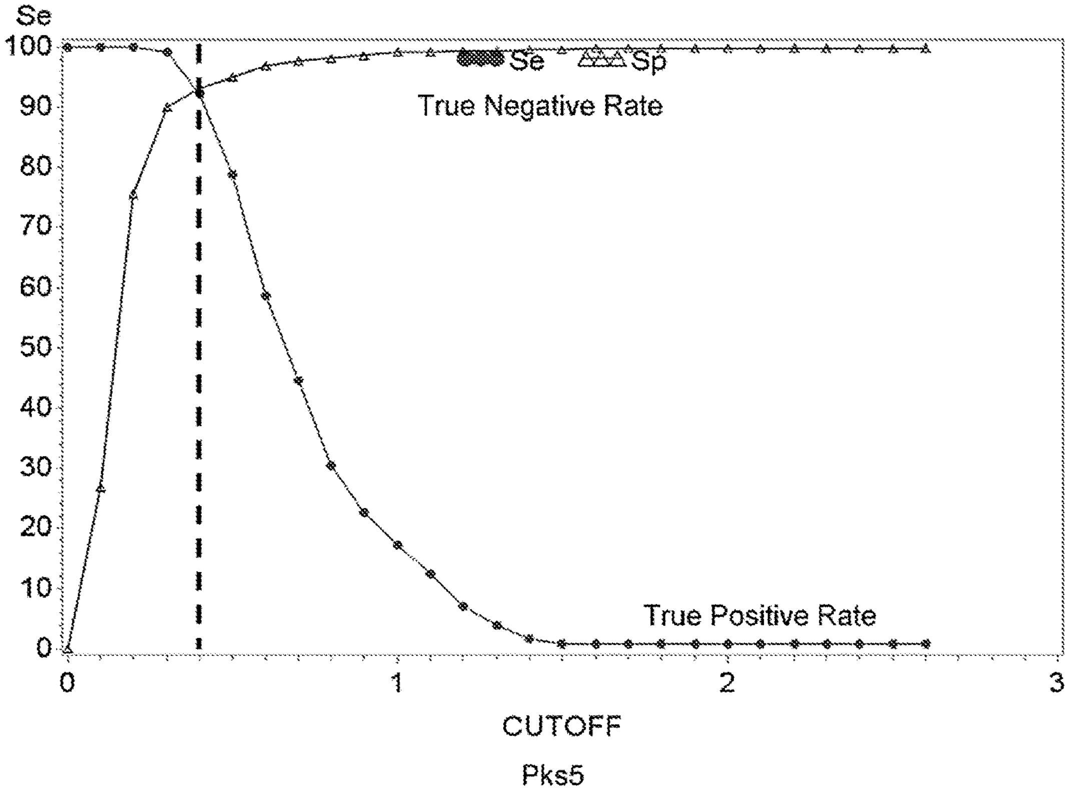
FIG. 6: Pks5 distinguished bovine tuberculosis positive and negative exposed animals. The true negative rate and true positive rate using Pks5 as a biomarker were plotted against each other. The optimal cutoff value corresponded to 0.4 nm. Cutoff value corresponds to a sensitivity of 92.2% and specificity of 93.2%.
Figure 7:
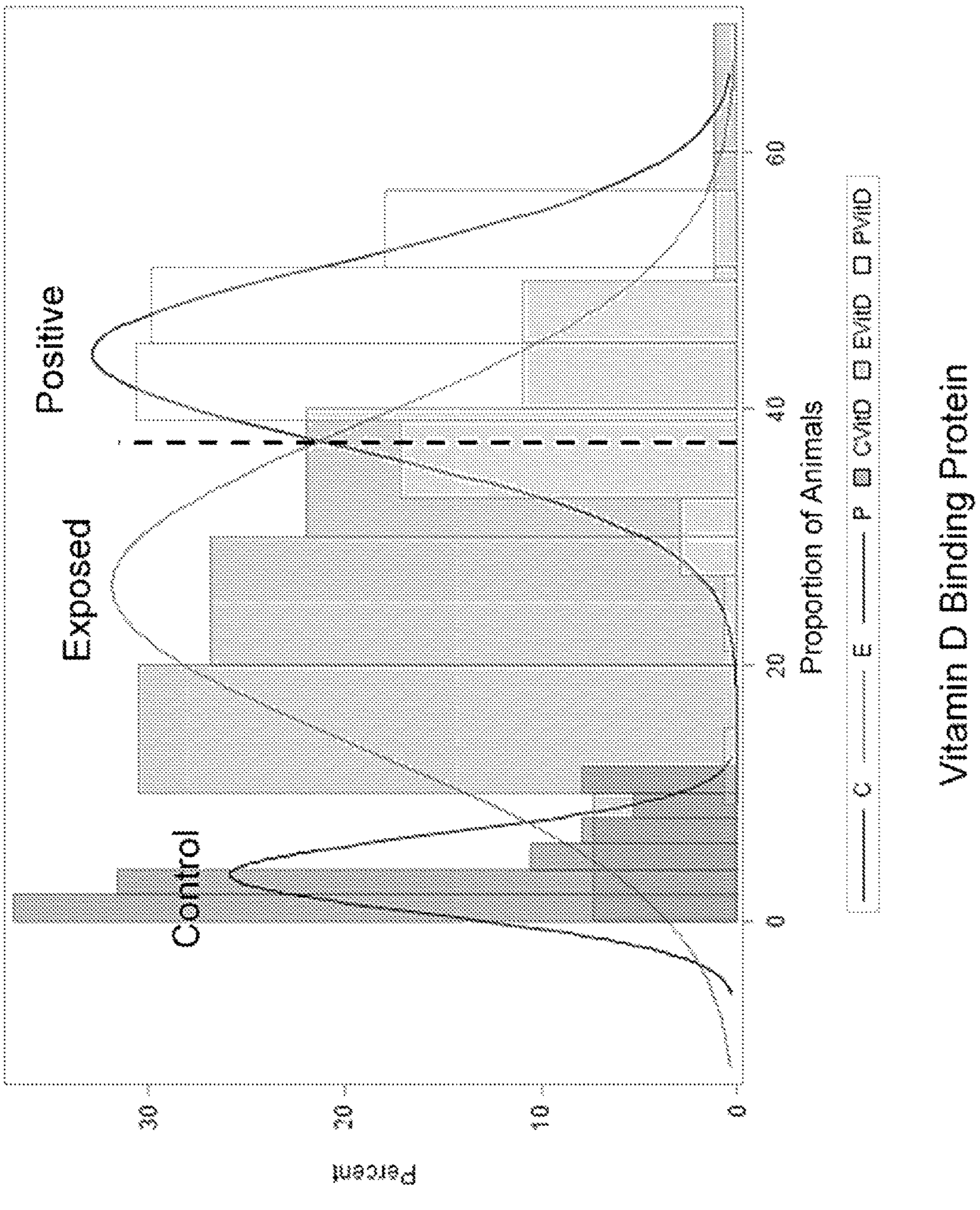
FIG. 7: Vitamin D binding protein (VDBP) histogram. Relative densities were collected from negative control (n=38), negative bTB exposed (n=82) and infected (n=128) animals. Cutoff value (38.50) was determined based on ROC analysis and true negative rate versus true positive rate. Control, positive and exposed groups showed clear separation.
Figure 8:
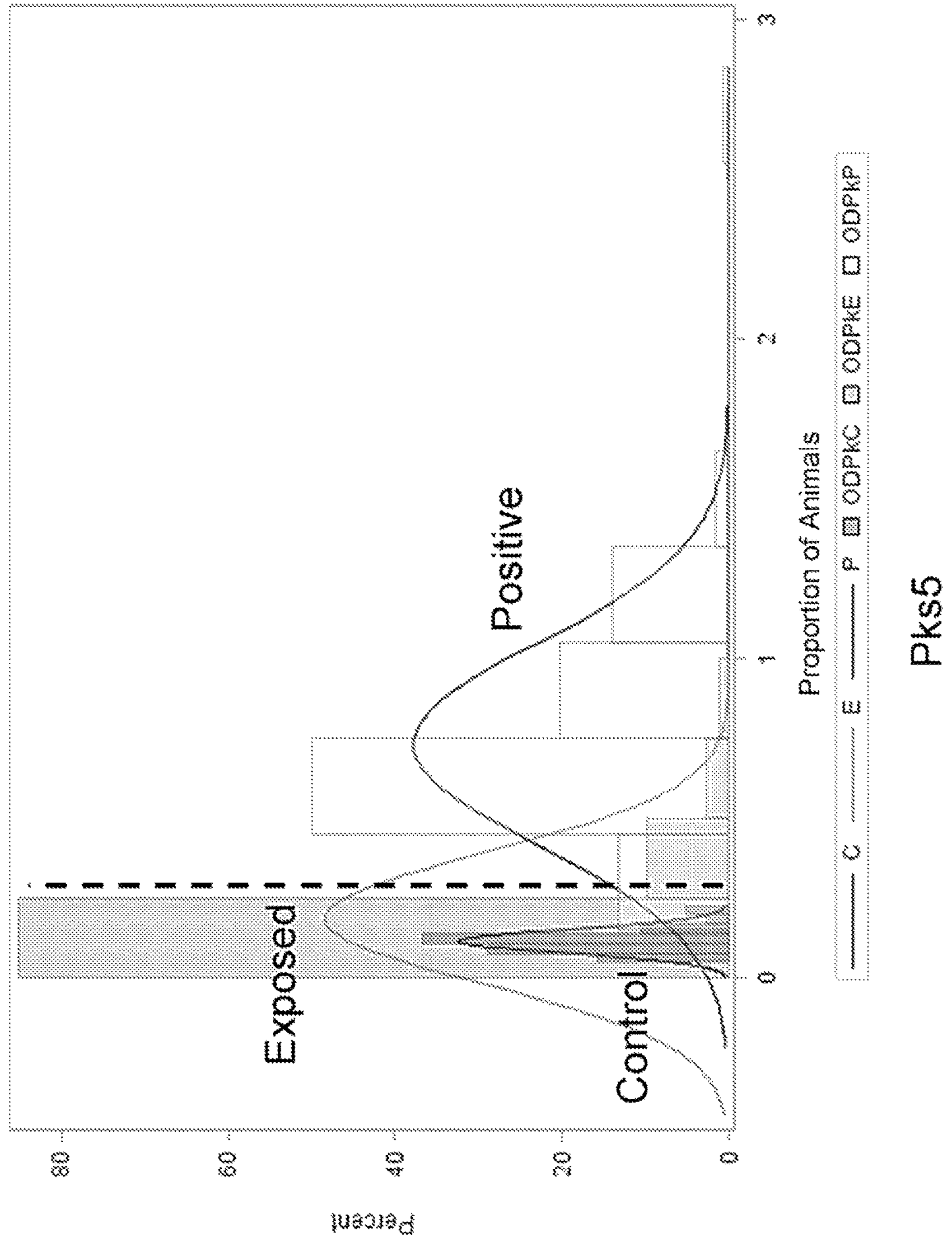
FIG. 8: Polyketide synthetase 5 (Pks5) histogram. Relative densities were collected from negative controls (n=38), negative bTB exposed (n=428) and infected (n=128) animals. Cutoff value (0.4 nm) was determined based on ROC analysis and true negative rate versus true positive rate.

*M. bovis* Proteins MB1895c, MB2515c and Pks5 are Present in bTB Positive and Exposed Animals Three *M. bovis* proteins (MB1895c, MB2515c, and Pks5) identified in iTRAQ analysis were selected for antibody production. Field (bTb [n=128], negative bTB exposed [n=428], and negative control [n=38]) animals were tested for detection with MB1895c, MB2515c, and Pks5 antibodies. AUC show that all three pathogen markers easily distinguish negative from infected animals (FIG. 4). Pks5 showed the greatest separation of bTB positive samples from negative bTB exposed and negative animals (FIG. 8). Cutoff values from ROC, true positive rate, and true negative rate analyses determined that the maximum sensitivity (92.2%) and specificity (93.2%) was achieved at 0.4 nm (FIGS. 4-6). MB1895c cutoff value that provided separation of exposed and infected animals while retaining a high degree of specificity was 0.3 nm. The MB2515c cutoff value of 0.2 had a sensitivity of 69.5% and specificity of 64.1%. Together these data show that circulating pathogen peptides are detected within *M. bovis* infected animal sera, which may be used to distinguish control, exposed, and infected cattle.

Application of Pks5 to Detect Bovine Tuberculosis in a Low Prevalence Region

Figure 9:
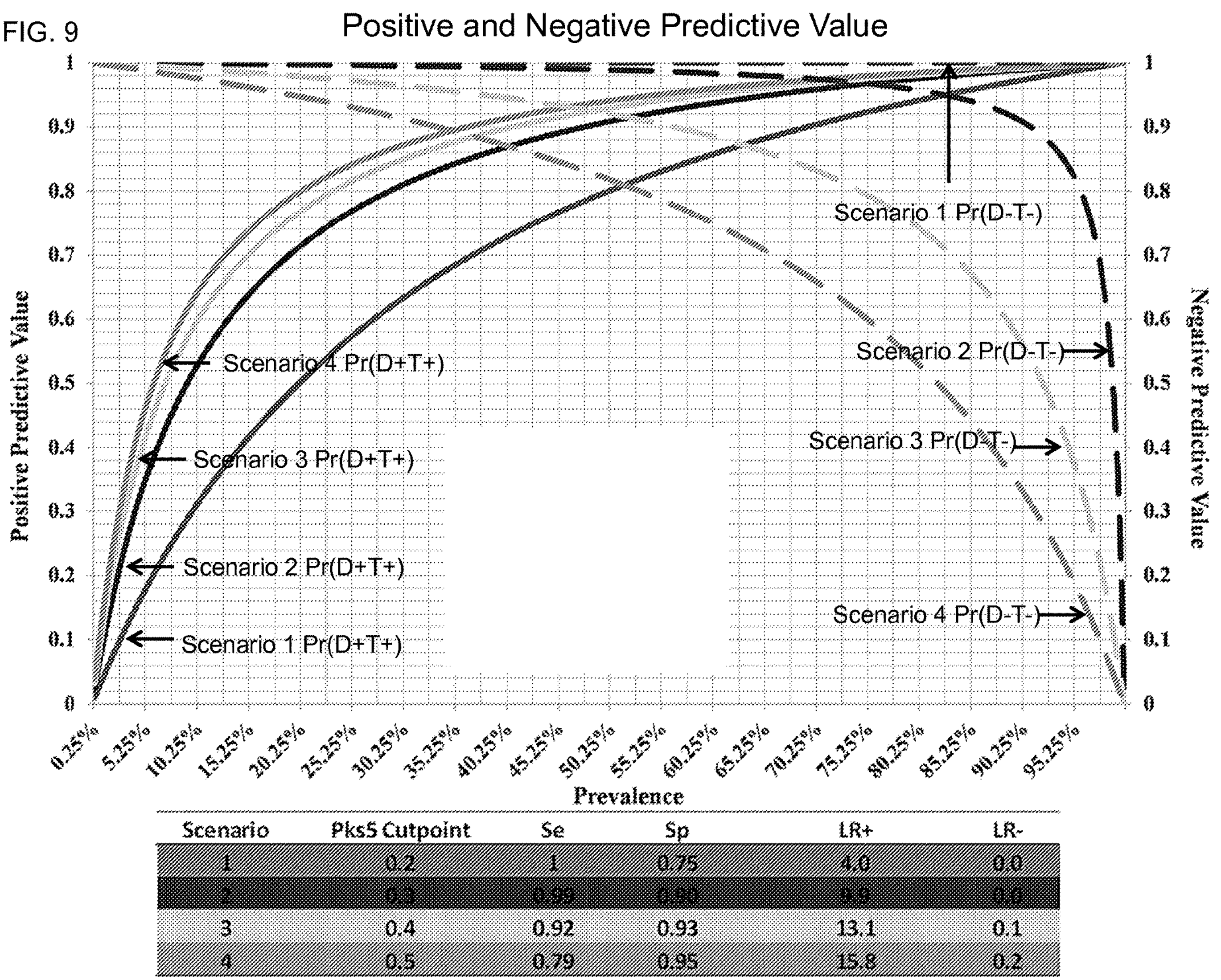
FIG. 9: Pks5 Positive and Negative Predictive Values and Cutoff Values Based on Bovine tuberculosis Prevalence. Positive and negative predictive values were plotted against percent prevalence. Cutoff values were assigned to 4 scenarios based on prevalence. Scenario 1=High bTB prevalence, Scenario 2=Moderate bTB prevalence, Scenario 3=Moderate-low bTB prevalence, and Scenario 4=Low bTB prevalence.

Many infectious disease diagnostics rely on a single cutoff value to indicate infectious status. However, diagnostic requirements may differ between regions of low and high prevalence for bTB. Therefore, we determined the positive and negative predictive values of Pks5 to correctly diagnose bTB given known disease prevalence of ~10% (FIGS. 2 and 3). In regions of high bTB prevalence, scenarios 1 and 2 would be applicable given increased sensitivity, while low prevalence areas would require increased specificity (scenarios 3 and 4) (FIG. 9). In order to determine the utility of Pks5 in a low prevalence bTB region and the possibility of cross-reactivity with other pathogenic mycobacteria, we tested sera from cattle infected with either *M. avium* subsp. *paratuberculosis* or *M. kansasii* and considered the cutoff value from scenario 4 (FIG. 9). Ninety percent of *M. avium* subsp. *paratuberculosis* and *M. kansasii* sera tested were categorized as uninfected animals under scenario 4 (low prevalence) and only 1 animal from each group was categorized as bTb infected. Data suggest that multi-cutoff value testing based on prevalence can provide bTB testing in various locations and that Pks5 is specifically shed. There is minimal Pks5 cross-reactivity to other pathogenic mycobacteria infections.

We tested three host serum proteins (VDPB, alpha-1-antitrypsin, and fetuin-A) and three pathogen proteins (MB2515c, MB1895c and Pks5) in a large-scale validation study using well-characterized field sera from *M. bovis* infected, negative bTB exposed, and negative controls. Reliance exclusively on host-related biomarkers of infectious disease can, however, provide indeterminate results. This may be due, at least in part, to cross-reactivity with similar pathogenic and environmental bacteria and/or other diseases (e.g., potentially of a non-infectious nature). We therefore interrogated iTRAQ datasets for *M. bovis*-specific proteins in infected animal sera. Pathogen proteins MB2515c, MB1895c, and Pks5, were present in all infected animal sera. All three proteins were capable of distinguishing *M. bovis* infected and suspect cases from uninfected controls. Although all three pathogen peptides easily separated negative from infected animals, this alone may not necessarily be adequate for all possible testing applications. For example, animals within a suspected bTB herd are likely to be of an exposed status (i.e., contact with infected animals) rather than a truly uninfected classification. Thus, comparisons between only bTB and negative animals could lead to an improperly low cutoff value that, when applied in the field, can produce a higher false positive rate. Therefore, we examined the ability of each pathogen protein to differentiate between infected and exposed animals (FIG. 4). Pks5 provided a high AUC and, therefore, the ability to distinguish between both (a) infected versus exposed animals, and (b) bTB and negative animals.

Current testing strategies are based on a single cutoff value to diagnosis bTB infection regardless of prevalence. Such a “one-size-fits-all” testing method is not necessarily appropriate for all testing applications. For example, in the United States, bTB affects less than 0.1% of all herds and diagnostics with a cutoff based on high sensitivity may incorrectly identify animals exposed to other mycobacteria (e.g. *M. avium* subsp. *paratuberculosis*) as bTB positive. This sort of misidentification can negatively impact the agricultural economy of a low prevalence area. In such scenarios, cutoff values can rely more on specificity than sensitivity. In contrast, areas with a high prevalence of bTB, such as China and India, it may be beneficial to have testing cutoffs that rely more on sensitivity than specificity in order to capture all infected cattle and minimize potential spillover to other animals and humans.

Pks5 proved to be an effective marker for testing methods that may employ more than one, or variable, cutoff values suitable for a particular application. We determined exemplary Pks5 cutoff values based on scenarios for high (scenarios 1 and 2) and low (scenarios 3 and 4) prevalence areas (FIG. 9).

To ensure that Pks5 did not react with other pathogenic mycobacteria, we tested sera from animals infected with *M. avium* subsp. *paratuberculosis* and *M. kansasii*. Pks5 exhibited limited cross-reactivity against *M. avium* subsp. *paratuberculosis*-infected and *M. kansasii*-infected sera.

Identification of *M. bovis* Lipids

We validated the presence of mannosylated lipoarabinomannan (ManLAM), a major mycobacterial cell wall glycolipid, in the serum of *M. bovis*-infected cattle. During the establishment and progression of *M. bovis* infection, mycobacterial-specific proteins and lipids, including those from the bacterial cell wall, are shed into host fluids. Lipoarabinomannan, which is a cell wall glycolipid found on pathogenic mycobacteria, can be detected in sera and urine of *M. bovis*-infected animals.

Fifty-five animals (uninfected [n=33], bTb [n=10] and exposed cases [n=12]) were screened for the presence of LAM using a commercially available ELISA. A LAM concentration curve was created and cross-reactivity to another glycolipid, non-capped lipoarabinomannan (AraLAM), found in environmental mycobacteria was assessed. AraLAM was not discernable from the kit negative control. Herds suspected of a bTB-positive status will likely include contact animals (exposed) rather than pristine animals (i.e., uninfected and unexposed). Therefore, ROC and AUC analyses compared bTB-positive and bTB-negative controls against bTB-exposed animals.

Figure 10:
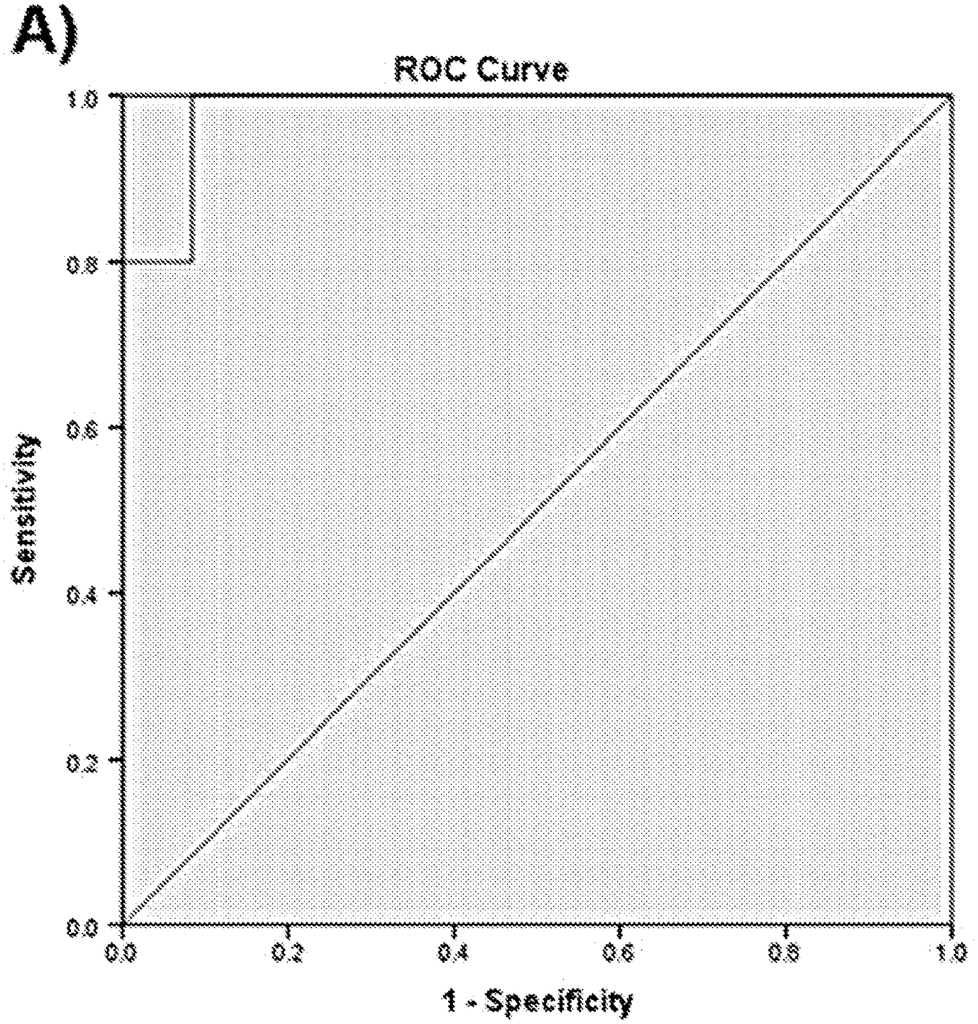
FIG. 10. Receiver operating characteristic (ROC) curves for LAM. (A) Each point on ROC curves is the fraction of bTB positive cattle (true-positive rate) versus the corresponding fraction of bTB exposed (false-positive rate) with an AUC of 0.983; (B) Each point on ROC curves is the fraction of exposed bTB cattle (true-positive rate) versus negative controls (false-positive rate) with an AUC of 0.949.
Figure 10:
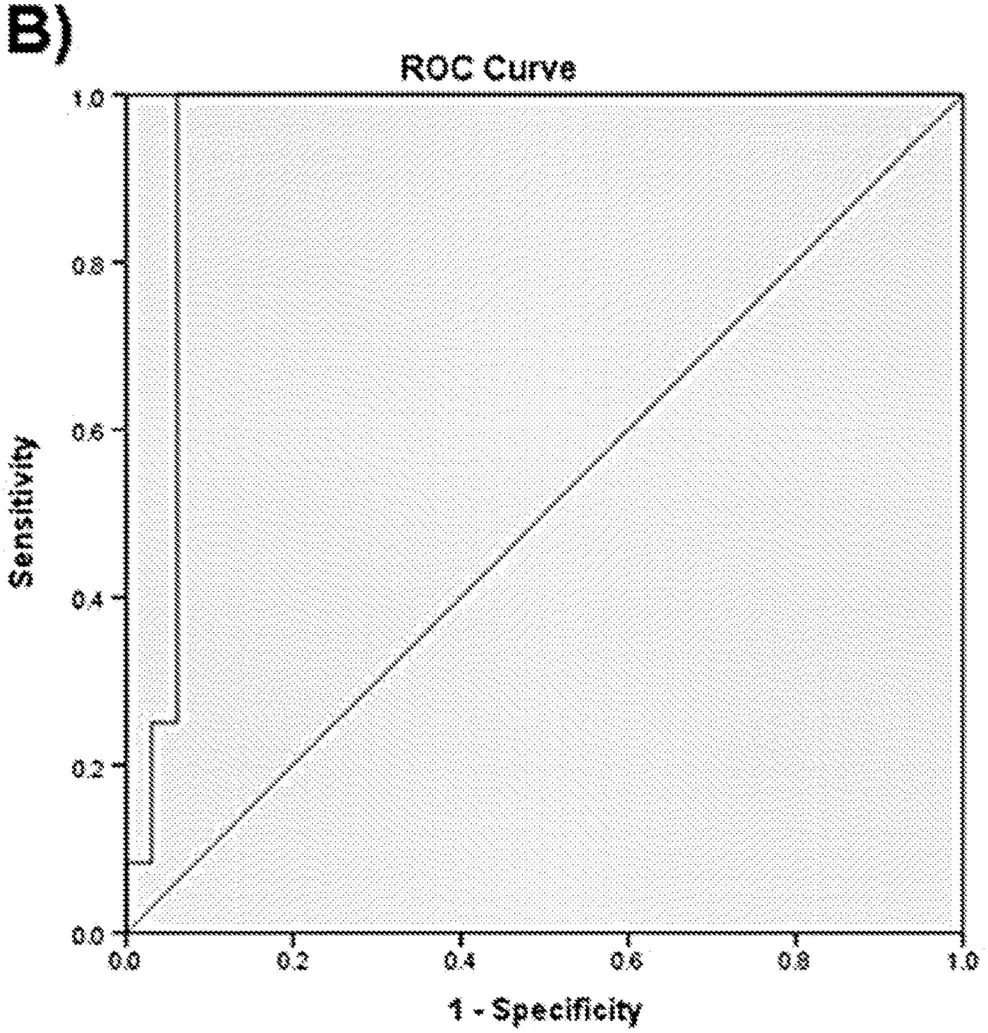

The AUC showed a near perfect separation for bTB-positive versus bTB-exposed animals (0.983) and bTB-exposed versus bTB-negative control animals (0.949) (FIG. 10A and FIG. 10B, respectively). Five cutoff ODs (0.3368-0.16089 nm) that retained high sensitivity and specificity were identified in bTB-positive and bTB-exposed comparison by ROC analysis. ROC analysis of bTB-exposed versus negative controls determined three cutoff ODs (0.0055-0.068 nm).

The true positive and negative rates were plotted against the OD cutoffs to determine optimal cutoff values. The optimal cutoff value was calculated at 0.7901 nm with a sensitivity of 100% and a specificity of 91.7% for bTB-positive versus bTB-exposed animals (FIG. 11A). The optimal cutoff value to distinguish bTB-exposed animals from negative controls was calculated at 0.0055 with a sensitivity of 100% and specificity of 93.9% (FIG. 11B). Together, these data indicate that the LAM ELISA can be effectively applied for rapid detection of *M. bovis* infection and exposure.

While detection systems utilizing host responses provided a first layer in identification of suspect diseased animals, they lack the needed specificity to eliminate cross-reactivity with other non-pathogenic mycobacteria or confusion with chronic illnesses of a non-infectious nature. This disclosure describes *M. bovis* peptides circulating in the serum accurately predict bTB-infected from bTB-negative and exposed animals. This disclosure further describes another *M. bovis* component, lipoarabinomannan (LAM), that is present in serum of bTB-infected animals. These *M. bovis* components may be used, either alone or with with additional pathogen signature components, to provide a battery test for subclinical bTB.

Figure 11:
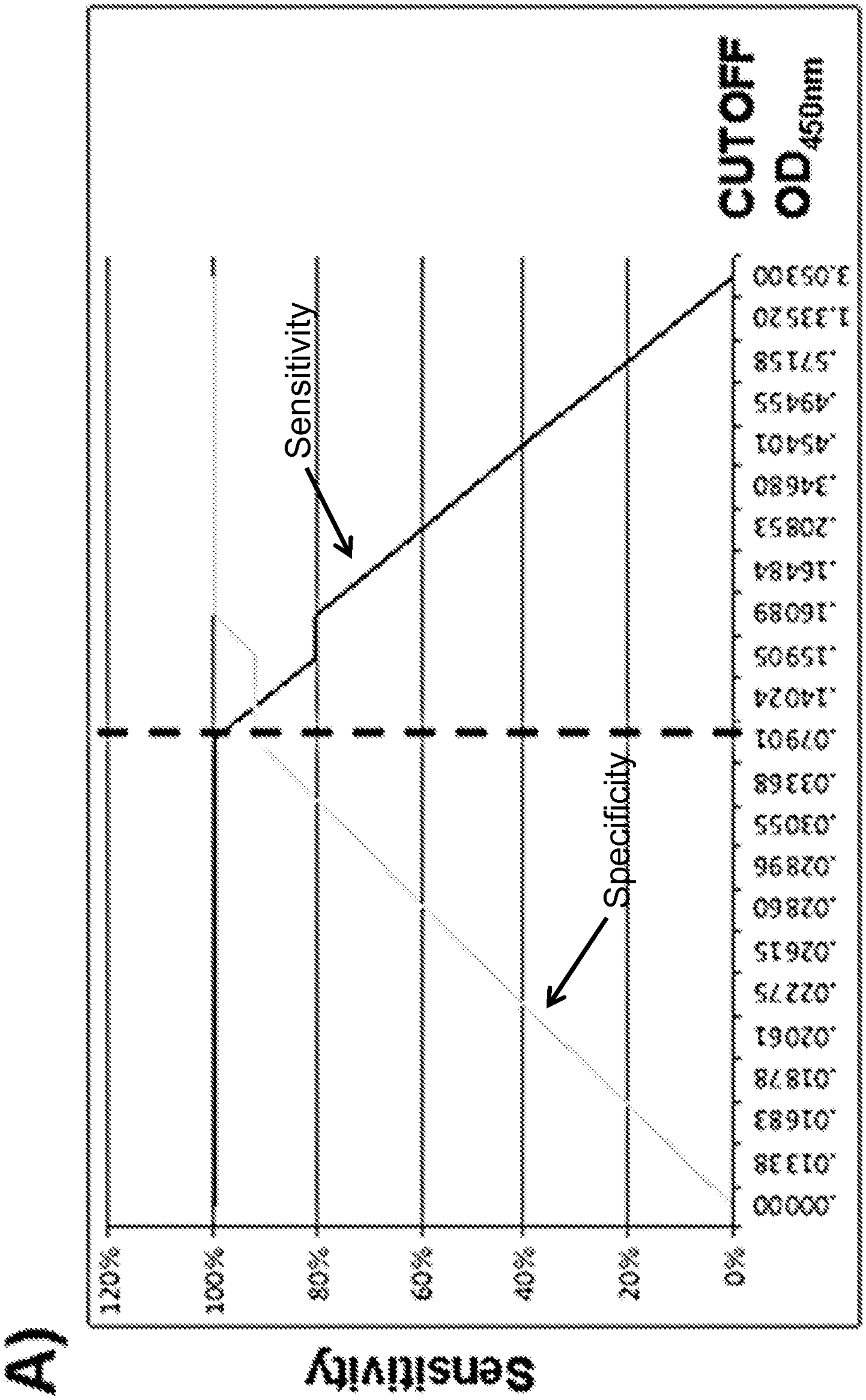
FIG. 11. LAM distinguishes bovine tuberculosis positive and negative controls and exposed animals. The true negative rate and true positive rate using LAM as a biomarker were plotted against each other. (A) The optimal cutoff value for bTB positive versus bTB exposed corresponds to O.D.$_{.450\ nm}$ of 0.7901 (100% sensitivity and 91.7% specificity); (B) The optimal cutoff value for bTB exposed versus negative controls corresponds to O.D.$_{.450\ nm}$ of 0.0055 (100% sensitivity and 93.9% specificity).
Figure 11:
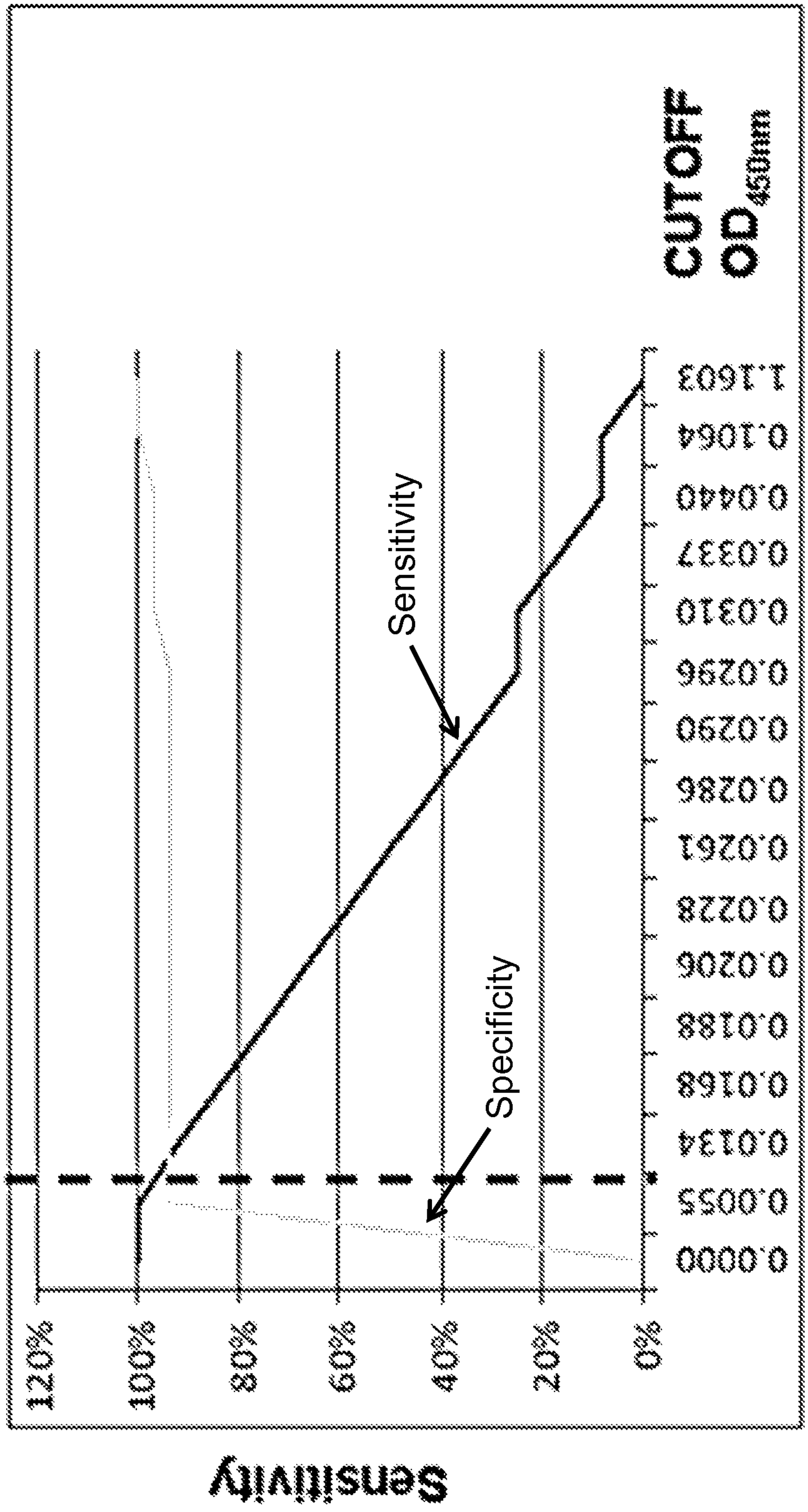

We show that the presence of LAM correlates with bTb infection and is capable of separating infected from bTB-exposed and bTB-negative animals. A single cutoff value applied to the true negative and positive rates showed LAM with a sensitivity of 100% and specificity of 91.7% for bTB positive versus bTB exposed animals (FIG. 11). The identification of a glycolipid in infected serum also opens the possibility for identification of other pathogen-related lipid biomarkers.

Although host and pathogen serum proteins have served as diagnostic biomarkers of *M. bovis* infection, conventional tests—in the form of, for example, dot blots and ELISAs—are not feasible in the field. A diagnostic test for field use should provide sensitivity (to limit false negative results), specificity (to limit false positive results), rapid results, and ease of testing. Analyzing a sample for these biomarkers using appropriate point of care testing device such as, for example, a nanosensor microfluidic apparatus or portable surfaced-enhanced Raman spectroscopy can provide improved convenience and throughput compared to detection methods using conventional lab-based *M. bovis* detection methods. As used herein, therefore, the term “point of care” can include, for example, field locations—i.e., a location geographically closer to the animal being tested than a laboratory and/or clinic.

Thus, this disclosure provides a method of detecting infection of a host by *M. bovis*. Generally, the method includes obtaining a biological sample from a host animal at risk of being infected by *Mycobacterium bovis*, and analyzing the sample for the presence or absence of at least one *M. bovis* polypeptide. In some embodiments, the method can further include analyzing the sample for the presence or absence of at least one *M. bovis* lipid.

In some embodiments, the biological sample can include any suitable biological material such as, for example, serum, plasma, urine, or fecal extracts.

In some embodiments, the *M. bovis* polypeptide being detected is adequate to distinguish a subclinical *M. bovis* infection from infection by other *Mycobacterium* species such as, for example, *M. avium* subsp. *paratuberculosis* or *M. kansasii*. Thus, in an area where another *Mycobacterium* species is prevalent, the method can be designed so that the *M. bovis* polypeptide does not cross-react with proteins from the other *Mycobacterium* species. In other embodiments, however, it may be acceptable to design the method using a *M. bovis* polypeptide that cross-reacts with a protein from another *Mycobacterium* species if that other *Mycobacterium* species is not expected to be present (e.g., is not natively present) in the area where the method is being performed.

In some embodiments, the method can include detecting one or more of MB1895c, MB2515c, MB0862, MB1482c, MB2883c, MB1929, MB1192 MB1886c, MB2441c, MB2275, MB2122c, MB1672c, MB3729c, MB1268, MB3017c, or Pks5.

In some embodiments, the method can include analyzing the sample for the presence or absence of at least one *M. bovis* lipid. In some cases, the *M. bovis* lipid being detected may be adequate to distinguish a subclinical *M. bovis* infect from infection by other *Mycobacterium* species such as, for example, *M. avium* subsp. *paratuberculosis* or *M. kansasii*. Thus, similar to embodiments that involve detecting the presence of a *M. bovis* polypeptide, in an area where another *Mycobacterium* species is prevalent, the method can be designed so that the *M. bovis* lipid does not cross-react with lipids produced by the other *Mycobacterium* species. In other embodiments, however, it may be acceptable to design the method using a *M. bovis* lipid that cross-reacts with a lipid from another *Mycobacterium* species if that other *Mycobacterium* species is not expected to be present (e.g., is not natively present) in the area where the method is being performed. In some embodiments, the *M. bovis* lipid can include lipoarabinomannan.

In some embodiments, the host animal may have, and the method may detect, a subclinical *M. bovis* infection. As used herein, the term “subclinical infection” refers to a status in which the host animal may harbor *M. bovis* microbes, but not yet manifest any symptoms or clinical signs of being infected by *M. bovis*. Consequently, in some embodiments, the method may be performed on a host who is or is at risk of being infected with *M. bovis*. “At risk” refers to a host that may or may not actually be infected with *M. bovis*. Thus, for example, a host “at risk” of infection by *M. bovis* is a host animal present in an area where individuals have been identified as infected by *M. bovis* and/or is likely to be exposed to *M. bovis* (e.g., the host is present within the known geographical range of *M. bovis*) even if the host has not yet manifested any detectable indication of infection by *M. bovis* and regardless of whether the host may harbor a subclinical amount of *M. bovis*. As used herein, the term “sign” or “clinical sign” refers to an objective physical finding relating to a particular condition capable of being found by one other than the patient; and the term “symptom” refers to any subjective evidence of disease or of a patient’s condition.

In some embodiments, the methods described herein may be used in combination with other methods, including other methods that are described herein. Thus, for example, the method can include analyzing a sample for the presence or absence of one or more *M. bovis* polypeptides and one or more *M. bovis* lipids. The methods described herein also may be combined with conventional methods of bTB detection. For example, the methods described herein may be used in the field to provide early detection so that, for example, appropriate preliminary quarantine procedures may be implemented, which can later be confirmed using conventional laboratory-based methods of bTB detection. The preliminary quarantine procedures can limit spread of *M. bovis* within a herd (or larger geographical area) while the bTB-positive result is confirmed, thereby reducing the extent of economic loss of a positive result.

As used herein, the term “use in the field” and variations thereof refer to tests that may be performed at point of care—i.e., at or near the location of the animals being tested rather than in a laboratory setting. Thus, in some embodiments, the methods described herein may be performed as an ELISA, dot blot assay, or any test format that involves lateral flow in a portable device. Such a “point of care” or “in the field” test can typically provide a result in, for example, 10-15 minutes. In contrast, a conventional γ-interferon release assay (IGRA) typically requires 5-6 hours and sophisticated laboratory equipment.

Thus, in some embodiments, the methods described herein can produce a result in a maximum time of no more than 250 minutes, such as, for example, no more than 230 minutes, no more than 200 minutes, no more than 180 minutes, no more than 150 minutes, no more than 120 minutes, no more than 90 minutes, no more than 60 minutes, no more than 50 minutes, no more than 40 minutes, no more than 30 minutes, no more than 25 minutes, no more than 20 minutes, or no more than 15 minutes. In some embodiments, the methods described herein can provide a result in a minimum time of no less than five minutes such as, for example, no less than 10 minutes, no less than 15 minutes, no less than 20 minutes, no less than 25 minutes, or no less than 30 minutes. In some embodiments, the methods described herein can provide a result with a range of time having endpoints defined be any maximum time listed above and any minimum time listed above that is less than the maximum time.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Sample Source.

All cattle used in this study were housed according to institutional guidelines and approved animal care protocols at the National Animal Disease Center (NADC; Ames, Iowa). Sera used for iTRAQ analyses were obtained from calves infected with *M. bovis* 95-1315 at the NADC. *M. bovis* infected calves were housed in a biosafety level 3 (BSL-3) facility. Sera were collected from *M. bovis* infected calves at baseline and prospectively for every month post-infection (PI) for five months. All calves were tested for disease associated immune response parameters, clinical signs and lesions characteristics identified at necropsy. Field samples from bTB infected and negative bTB exposed, *M. avium* subsp. *paratuberculosis*-infected, and *M. kansasii*-infected cattle (19, 22) were obtained from serum repositories at the National Veterinary Services Laboratory (NVSL; United States Department of Agriculture, Ames, Iowa) and National Animal Disease Center (NADC, USDA, Ames, Iowa), respectively. bTB infection status of each animal was confirmed by a combination of antemortem caudal fold tests, pathogen culture and lesion histology at necropsy. Negative controls were collected from bTB free dairy herds in Minnesota.

iTRAQ Data Analysis and Interpretation.

In our previous study, sera from *M. bovis* (n=5), *M. avium* subsp. *paratuberculosis* (n=5) infected calves and contemporary controls (n=5) were pooled in equal concentrations (100 μL of 100 μg/μL) and used in four individual iTRAQ experiments: 1) *M. bovis* infection versus contemporary controls; 2) *M. bovis* infection versus *M. avium* subsp. *paratuberculosis* infection; 3) early chronic *M. avium* subsp. *paratuberculosis* infection; and 4) late chronic *M. avium* subsp. *paratuberculosis* infection, as previously described. (Seth et al. 2009. *PLoS One* 4:e5478).

Host-specific peptides and relative abundance (>95% Confidence Interval (CI)) were identified using ProteinPilot software™ 2.0 and 2.01 (Applied Biosystems Inc., Foster City, Calif.) and the nr_bos_CTM_20070802 FASTA database. Pathogen peptides were identified using the *M. bovis* strain AF2122/97 genome. At least two unique peptides per protein were used as a cutoff for analysis ($P<0.05$ and an error factor (EF) of <2). The EF signifies the 95% CI for an average ratio of ($EF=10^{95\%\ CI}$, where 95% CI=(ratio×EF)−(ratio/EF)).

Immunoblotting for Host Response Associated Biomarkers During bTB Infection.

All procedures were developed at room temperature (RT). Field samples (n=128 confirmed bTB infected and n=82 negative bTB exposed) and negative controls (n=38) were spotted in duplicate and dried on 0.2 μm nitrocellulose membranes. Nitrocellulose membranes were blocked using 1× phosphate buffered saline (PBS)-0.05% Tween-20 (TW20) containing 5% nonfat dried milk powder for 1 h with subtle shaking and washed 5 times in 1×PBS-TW20 in 5 min increments. Nitrocellulose membranes were separately incubated with rabbit polyclonal α-1-antitrypsin (Abcam, Cambridge, Mass.), goat polyclonal fetuin-A (M-17) (Santa Cruz Biotechnology, Inc., Dallas, Tex.), and mouse anti-human VDBP (R&D systems, Minneapolis, Minn.)

diluted 1:1,000 in PBS-TW20 containing 1% nonfat dried milk powder for one hour with shaking and subsequently washed as described above. Binding of primary antibodies to sera was detected using a 1:10,000 dilution of anti-rabbit IgG (R&D systems, Minneapolis, Minn.), anti-mouse IgG (R&D systems, Minneapolis, Minn.) and anti-goat IgG (SantaCruz Biotechnology, Inc., Dallas, Tex.) conjugated to horseradish peroxidase (HRP) incubated for one hour with shaking followed by 5 PBS-TW20 washes and development with Western Lightening Enhanced Chemiluminescence substrate (PerkinElmer, Waltham, Mass.) per manufacturer's instructions. Membranes were imaged using simple biochem acquisition from Labworks 4.6 software (Labworks Inc., Costa Mesa, Calif.) and raw density values were calculated.

Production of Monoclonal Antibodies Against *M. bovis* Specific Peptides Present in the Serum of Animals Infected with *M. bovis*.

MB2515c, MB1895c, and MB1554c (Pks5) antibodies were commercially produced by NEOBioscience (Cambridge, Mass.). Proteins were selected based on iTRAQ identification and potential for immunogenicity. Briefly, peptides were designed for each protein using NEOBioscience software that considered hydrophilicity, flexibility, accessibility, rotation, surface exposed probability and antigenicity. A Basic Local Alignment Search Tool (BLAST) was performed on *M. bovis* proteins to eliminate homologous sequences. Mice (n=5 for each peptide) were initially injected intraperitoneally with an emulsion of peptide (10-50 μg) and Complete Freund's Adjuvant (CFA, add source) in sterile saline. Immunizations were repeated 2 times using Incomplete Freund's Adjuvant (IFA, add source) and once using PBS in place of CFA in 14 and 21 day intervals post-immunization. Every 21 days post-immunization blood was drawn from mice and tested against appropriate peptides using indirect ELISA. All mice were euthanized 61 days post-immunization and spleens were harvested for splenocyte extraction. Splenocytes were fused with hybridomas, which were seeded into individual wells in a 96 well plate and screened by ELISA to detect positive clones. Clones 19-1-1 (MB1895c), 5-1-3 (Pks5) and 3-1-2 (MB2515c) were selected, subcloned by limiting dilution, and isotyped. Clones were expanded and the supernatant was collected. Monoclonal antibodies were kept at −70° C. until further use.

Development of an Indirect ELISA to Detect *M. bovis*-specific Peptides in Serum.

bTB confirmed (n=128), bTB negative exposed (n=424), *M. kansasii*-infected (n=10), *M. avium* subsp. *paratuberculosis*-infected (n=10), and negative control sera (n=38) were individually diluted in 0.05 M carbonate-bicarbonate buffer (pH=9.6; Sigma-Aldrich, St. Louis, Mo.) at a 1:50 (MB1895c and MB2515c detection) and 1:100 dilution (Pks5 detection) and 50 μL/well of each sample was transferred to separate wells in Nunc Maxisorp flat bottom ELISA plates. Each sample was plated in triplicate. Sera were allowed to absorb overnight at 4° C. and plates were washed three times using 200 μL/well of PBS. Plates were blocked in 200 μL/well of Blocker™ BLOTTO in Tris-buffered saline (TBS) (Pierce, Rockford, Ill.) for two hours at 37° C., washed three times using 300 μL/well of 1× Femto PBS containing 0.05% TW20 (G-Biosciences, St. Louis, Mo.), and incubated with either 100 μL/well of a 1:5,000 dilution of MB2515c or MB1895c or a 1:10,000 dilution of Pks5 resuspended in a 1% solution of Blocker™ BLOTTO in TBS with 0.05% TW20 for one hour at room temperature. Plates were washed as described above and incubated with 100 μL/well of goat anti-mouse IgG-HRP (Santa Cruz Biotechnology, Inc., Dallas, Tex.) diluted 1:5,000 in 1% Blocker™ BLOTTO in TBS with 0.05% TW20 for one hour at room temperature and subsequently washed. ELISA plates were developed with 100 μL/well of 1-Step™ Ultra TMB-ELISA (Pierce, Rockford, Ill.) and incubated for 30 minutes at room temperature in the dark. TMB reaction was stopped with the addition of 50 μL/well of 2 M sulfuric acid and optical densities were recorded at 450 nm using the SpectraMax M2 microplate reader and software (Molecular Devices, Sunnyvale, Calif.). Positive cut-off values were calculated from the negative control average and two standard deviations.

Statistical Analysis.

To construct receiver operating characteristic (ROC) curves for each biomarker, test results in each individual animal were averaged across replicates and the respective coefficient of variation calculated (Supplemental information). ROC curves for host response and *M. bovis* specific biomarkers were compared using the area under the ROC curve (AUC). Two comparisons were performed, positive versus within herd exposed negative controls (exposed) and positive versus not exposed negative controls (controls). For the best biomarker in each class, sensitivity (Se) and specificity (Sp) values were calculated at optimal cutoff values. For the best performing biomarker, positive (PPV) and negative predictive values (NPV) with respective cutpoint specific likelihood ratios (LR) were calculated at four different optimal combinations of Se and Sp, in order to develop a framework for a decision analysis algorithm in multiple scenarios of disease prevalence (Dohoo et al. 2010. Veterinary Epidemiologic Research. VER Inc.). ROC curves and sensitivity-specificity plots were generated using SAS 9.3 (SAS Institute Inc., Cary, N.C., USA).

Example 2

Sample Source

Field samples from bovine tuberculosis infected and exposed cases were generously provided by the National Veterinary Services Laboratory (NVSL; United States Department of Agriculture, Ames, Iowa) serum repositories. All field samples were collected from a single herd in California. Bovine tuberculosis disease status for each animal was validated using a combination of bacterial culture, antemortem caudal fold tests (CFT) and lesion histology at necropsy. Johne's disease history for this herd was indeterminate. Bovine tuberculosis exposed cases were defined as animals that had contact with bovine tuberculosis infected animals but remained bovine tuberculosis negative (i.e. negative results for culture, CFT and histology). Negative controls were collected from a bovine tuberculosis free dairy herd in Minnesota. Negative controls tested negative for *M. bovis* (culture, histology, and CFT).

Lipoarabinomannan Enzyme-linked Immunosorbent Assay (ELISA)

Randomly selected field sera samples (bTB positive n=10 and bTB exposed n=12), negative controls (n=33), and negative controls spiked with either *M. tuberculosis* strain H37Rv purified mannosylated lipoarabinomannan (ManLAM) (BEI Resources; NR-14848) or *M. smegmatis* purified non-mannose-capped lipoarabinomannan (AraLAM) (BEI Resources; NR-14849) (Biodefense and Emerging Infections Research Resources Repository, NIAID, NIH) were diluted 1:5 in PBS and analyzed for the presence of LAM using the human LAM ELISA kit (Biotang, Waltham, Mass.) according to the manufacturer's instructions. A LAM standard curve was included using kit controls and two-fold dilution series of ManLAM spiked sera. The standard curve was plotted using GraphPad Prism software (GraphPad Software, LaJolla, Calif.). The optical density was read at 450 nm with a wavelength correction at 570 nm. All samples were read in three wells. LAM ELISA was repeated twice.

Statistical Analysis

Optical densities for each animal were averaged across the replicates. Receiver operating characteristic (ROC) curves were compared for 1) positive versus within-herd negative exposed (exposed) and 2) positive versus negative controls using the area under the ROC curves (AUC). Optimal cutoff values were determined by maximizing specificity and sensitivity by plotting the true negative rate against the true positive rate. ROC curves and specificity-sensitivity plots were created in SPSS® (IBM Corp. Released 2013, IBM SPSS Statistics for Windows, Version 22.0, Amonk, N.Y.).

EXEMPLARY EMBODIMENTS

Embodiment 1

A method comprising: obtaining a biological sample from a host animal at risk of being infected by *Mycobacterium bovis*; and analyzing the sample for the presence or absence of at least one *M. bovis* polypeptide.

Embodiment 2

A method comprising: obtaining a biological sample from a host animal at risk of being infected by *Mycobacterium bovis*; and analyzing the sample for the presence or absence of at least one *M. bovis* lipid.

Embodiment 3

The method of Embodiment 1 further comprising analyzing the sample for the presence or absence of at least one *M. bovis* lipid.

Embodiment 4

The method of Embodiment 1 or Embodiment 3 wherein the *M. bovis* polypeptide does not cross-react with serum from a host animal exposed to another *Mycobacterium* spp.

Embodiment 5

The method of Embodiment 4 wherein the other *Mycobacterium* spp. comprises *M avium* subsp. *paratuberculosis.*

Embodiment 6

The method of Embodiment 4 wherein the other *Mycobacterium* spp. comprises *M. kansasii.*

Embodiment 7

The method of Embodiment 1 or Embodiment 3 wherein the *M. bovis* polypeptide comprises MB1895c, MB2515c, MB0862, MB1482c, MB2883c, MB1929, MB1192 MB1886c, MB2441c, MB2275, MB2122c, MB1672c, MB3729c, MB1268, MB3017c, or Pks5.

Embodiment 8

The method of Embodiment 2 or Embodiment 3 wherein the *M. bovis* lipid does not cross-react with serum from a host animal exposed to another *Mycobacterium* spp.

Embodiment 9

The method of Embodiment 8 wherein the other *Mycobacterium* spp. comprises *M. avium* subsp. *paratuberculosis.*

Embodiment 10

The method of Embodiment 8 wherein the other *Mycobacterium* spp. comprises *M. kansasii.*

Embodiment 11

The method of any one of Embodiments 2, 3, or 8-10 wherein the *M bovis* lipid comprises lipoarabinomannan.

Embodiment 12

The method of any preceding Embodiment wherein the biological sample comprises serum, plasma, urine, or a fecal extract.

Embodiment 13

The method of any preceding Embodiment wherein the host animal has a subclinical *M. bovis* infection.

Embodiment 14

The method of any preceding Embodiment wherein the host animal exhibits no symptoms or clinical sign of infection by *M. bovis.*

Embodiment 15

The method of any preceding Embodiment performed at point of care.

Embodiment 16

The method of Embodiment 15 performed using a microfluidic device.

Embodiment 17

The method of Embodiment 15 performed using portable surface-enhanced Raman spectroscopy.

Embodiment 18

The method of any preceding Embodiment further comprising detecting at least one host polypeptide whose expression is greater in a host infected with *M. bovis* compared to expression in a host known to be uninfected with *M. bovis.*

Embodiment 19

The method of Embodiment 18 wherein the host polypeptide comprises vitamin D binding protein (VDBP), fetuin-A.

As used herein, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

The complete disclosure of all patents, patent applications, and publications, and electronically available material cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method comprising:
obtaining a biological sample from a host animal at risk of being infected by *Mycobacterium bovis;*
analyzing the sample for the presence or absence of at least one *M bovis* lipid; and
detecting at least one *M bovis* polypeptide in the biological sample.

2. A method comprising:
obtaining a biological sample from a host animal at risk of being infected by *Mycobacterium bovis*; and
detecting at least one *M. bovis* lipid in the biological sample.

3. The method of claim 1 wherein at least one detected *M bovis* polypeptide does not cross-react with serum from a host animal exposed to a second *Mycobacterium* spp.

4. The method of claim 3 wherein the second *Mycobacterium* spp. comprises *M avium* subsp. paratuberculosis.

5. The method of claim 3 wherein the second *Mycobacterium* spp. comprises *M kansasii.*

6. The method of claim 1 wherein the *M. bovis* polypeptide comprises MB1895c, MB2515c, MB0862, MB1482c, MB2883c, MB1929, MB1192, MB1886c, MB2441c, MB2275, MB2122c, MB1672c, MB3729c, MB1268, MB3017c, or Pks5.

7. The method of claim 2 wherein at least one detected *M bovis* lipid does not cross-react with serum from a host animal exposed to a second *Mycobacterium* spp.

8. The method of claim 7 wherein the second *Mycobacterium* spp. comprises *M avium* subsp. *paratuberculosis.*

9. The method of claim 7 wherein the second *Mycobacterium* spp. comprises *M kansasii.*

10. The method of claim 2 wherein the *M bovis* lipid comprises lipoarabinomannan.

11. The method of claim 1 wherein the biological sample is serum, plasma, urine, or a fecal extract.

12. The method of claim 1 wherein the host animal has a subclinical *M bovis* infection.

13. The method of claim 1 wherein the host animal exhibits no symptoms or clinical sign of infection by *M bovis.*

14. The method of claim 1 performed at point of care.

15. The method of claim 14 performed using a microfluidic device.

16. The method of claim 14 performed using portable surface-enhanced Raman spectroscopy.

17. The method of claim 1 further comprising detecting at least one host polypeptide whose expression is greater in a host infected with *M bovis* compared to expression in a host known to be uninfected with *M bovis.*

18. The method of claim 17 wherein the host polypeptide comprises vitamin D binding protein (VDBP) or fetuin-A.

19. A method comprising:
obtaining a biological sample from a host animal at risk of being infected by *Mycobacterium bovis*; and
detecting at least one *M bovis* polypeptide in the biological sample, wherein at least one detected *M bovis* polypeptide does not cross-react with serum from a host animal exposed to a second *Mycobacterium* spp.

20. The method of claim 19 wherein the second *Mycobacterium* spp. comprises *M avium* subsp. *paratuberculosis.*

21. The method of claim 19 wherein the second *Mycobacterium* spp. comprises *M kansasii.*

22. The method of claim 19 wherein the *M. bovis* polypeptide comprises MB1895c, MB2515c, MB0862, MB1482c, MB2883c, MB1929, MB1192, MB1886c, MB2441c, MB2275, MB2122c, MB1672c, MB3729c, MB1268, or MB3017c.

23. The method of claim 19 further comprising detecting at least one host polypeptide whose expression is greater in a host infected with *M bovis* compared to expression in a host known to be uninfected with *M bovis.*

24. The method of claim 23 wherein the host polypeptide comprises vitamin D binding protein (VDBP) or fetuin-A.

25. The method of claim 19 wherein the biological sample is serum, plasma, urine, or a fecal extract.

26. The method of claim 19 wherein the host animal has a subclinical *M bovis* infection.

27. The method of claim 19 wherein the host animal exhibits no symptoms or clinical sign of infection by *M bovis.*

28. The method of claim 19 performed at point of care.

29. The method of claim 28 performed using a microfluidic device.

30. The method of claim 28 performed using portable surface-enhanced Raman spectroscopy.

31. The method of claim 2 wherein the biological sample is serum, plasma, urine, or a fecal extract.

32. The method of claim 2 wherein the host animal has a subclinical *M bovis* infection.

33. The method of claim 2 wherein the host animal exhibits no symptoms or clinical sign of infection by *M bovis*.

34. The method of claim 2 performed at point of care.

35. The method of claim 34 performed using a microfluidic device.

36. The method of claim 34 performed using portable surface-enhanced Raman spectroscopy.

* * * * *